United States Patent
Punga et al.

(10) Patent No.: US 9,999,501 B2
(45) Date of Patent: Jun. 19, 2018

(54) VALVE PROSTHESIS

(75) Inventors: Karan Punga, Santa Rosa, CA (US);
Finn Rinne, Santa Rosa, CA (US);
Donna Barrett, Ballybrit (IE)

(73) Assignee: Medtronic CV Luxembourg S.A.R.L., Luxembourg (LU)

( * ) Notice: Subject to any disclaimer, the term of this patent is extended or adjusted under 35 U.S.C. 154(b) by 502 days.

(21) Appl. No.: 13/449,863

(22) Filed: Apr. 18, 2012

(65) Prior Publication Data
US 2013/0282113 A1 Oct. 24, 2013

(51) Int. Cl.
*A61F 2/24* (2006.01)
*A61F 2/95* (2013.01)

(52) U.S. Cl.
CPC .......... *A61F 2/2418* (2013.01); *A61F 2/2436* (2013.01); *A61F 2002/9505* (2013.01); *A61F 2230/008* (2013.01); *A61F 2230/0013* (2013.01); *A61F 2230/0078* (2013.01)

(58) Field of Classification Search
CPC ............................ A61F 2/2418; A61F 2/2475
USPC ...................... 623/1.24, 1.26, 2.12–2.19, 900
See application file for complete search history.

(56) References Cited

U.S. PATENT DOCUMENTS

| | | | | |
|---|---|---|---|---|
| 6,458,153 B1 * | 10/2002 | Bailey et al. | ................ | 623/1.24 |
| 8,128,686 B2 * | 3/2012 | Paul et al. | ................... | 623/1.35 |
| 2006/0259136 A1 | 11/2006 | Nguyen et al. | | |
| 2009/0216312 A1 * | 8/2009 | Straubinger | .......... | A61F 2/2418 623/1.16 |
| 2009/0248132 A1 * | 10/2009 | Bloom | ................. | A61F 2/2418 623/1.15 |
| 2010/0094411 A1 | 4/2010 | Tuval et al. | | |
| 2011/0022157 A1 * | 1/2011 | Essinger | ............... | A61F 2/2418 623/1.26 |
| 2011/0264196 A1 * | 10/2011 | Savage et al. | ............... | 623/1.26 |
| 2011/0295361 A1 * | 12/2011 | Claiborne, III | ....... | A61F 2/2412 623/1.26 |
| 2012/0271398 A1 * | 10/2012 | Essinger et al. | ............. | 623/1.11 |
| 2013/0274870 A1 * | 10/2013 | Lombardi | ............. | A61F 2/2418 623/2.11 |
| 2014/0018915 A1 * | 1/2014 | Biadillah | .............. | A61F 2/2418 623/2.17 |
| 2014/0039614 A1 * | 2/2014 | Delaloye | ............... | A61F 2/2418 623/2.36 |

FOREIGN PATENT DOCUMENTS

| | | | |
|---|---|---|---|
| EP | 2428189 A1 | 3/2012 | |
| WO | WO2009/024859 | 2/2009 | |
| WO | WO2009/053497 | 4/2009 | |
| WO | WO 2010049160 A1 * | 5/2010 | ........... A61F 2/2412 |
| WO | 2011/051043 A1 | 5/2011 | |
| WO | 2011/109450 A2 | 9/2011 | |
| WO | 2011/137531 A1 | 11/2011 | |
| WO | 2013/078497 A1 | 6/2013 | |

* cited by examiner

*Primary Examiner* — Paul Prebilic
(74) *Attorney, Agent, or Firm* — Medler Ferro Woodhouse & Mills

(57) ABSTRACT

Heart valve prostheses are provided having a self-expanding frame that supports a valve body comprising a skirt and a plurality of coapting leaflets. The self-expanding frame includes an inflow section, a valve section, and an outflow section. The outflow section forms attachment loops in a collapsed configuration to attach the frame to a delivery system.

15 Claims, 12 Drawing Sheets

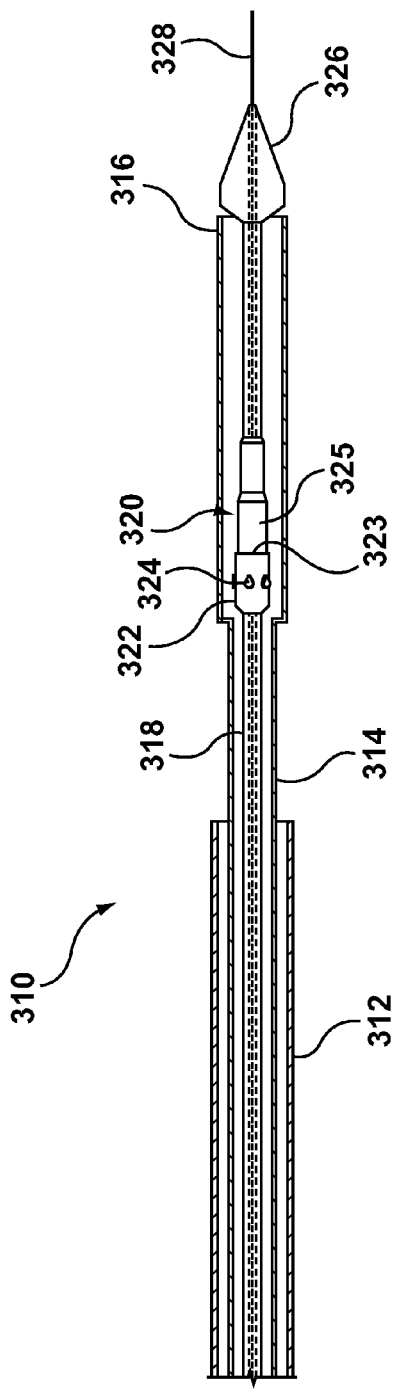
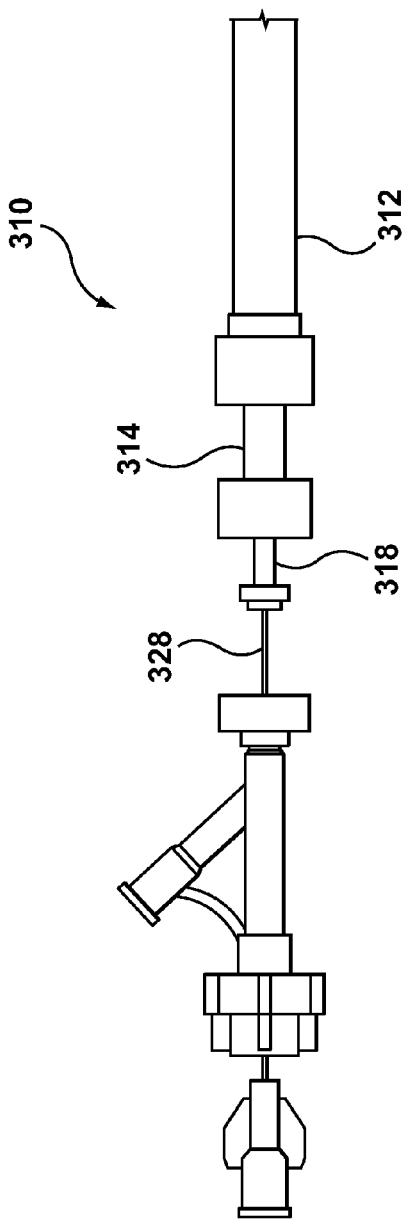
FIG. 4
FIG. 5

VALVE PROSTHESIS

BACKGROUND OF THE INVENTION

Field of the Invention

The present invention is related to artificial heart valves. More specifically, the present invention is directed to an artificial valve prosthesis.

Background Art

Cardiac valves exhibit two types of pathologies: regurgitation and stenosis. Regurgitation is the more common of the two defects. Either defect can be treated by a surgical repair. Under certain conditions, however, the cardiac valve must be replaced. Standard approaches to valve replacement require cutting open the patient's chest and heart to access the native valve. Such procedures are traumatic to the patient, require a long recovery time, and can result in life threatening complications. Therefore, many patients requiring cardiac valve replacement are deemed to pose too high a risk for open heart surgery due to age, health, or a variety of other factors. These patient risks associated with heart valve replacement are lessened by the emerging techniques for minimally invasive valve repair, but still many of those techniques require arresting the heart and passing the blood through a heart-lung machine.

Efforts have been focused on percutaneous transluminal delivery of replacement cardiac valves to solve the problems presented by traditional open heart surgery and minimally-invasive surgical methods. In such methods, a valve prosthesis is compacted for delivery in a catheter and then advanced, for example, through an opening in the femoral artery and through the descending aorta to the heart, where the prosthesis is then deployed in the aortic valve annulus.

In view of the foregoing, it would be desirable to provide a valve prosthesis that is capable of conforming to a patient's anatomy while providing a uniform degree of rigidity and protection for critical valve components. Protection for critical valve components is essential to maintain reliability for the valve prosthesis.

BRIEF SUMMARY OF THE INVENTION

Provided herein are valve prostheses that generally include a self-expanding frame, where the valve prosthesis is sutured to the self-expanding frame. Such configurations achieve numerous goals. For example, such configurations can: prevent the native leaflets from obstructing flow through the left ventricular outflow tract (LVOT); prevent the native leaflets from interacting with the prosthetic leaflets; recruit the native leaflets in minimizing perivalvular leaks; maintain proper alignment of the valve prosthesis; avoid systolic anterior mobility; and maintain valve stability by preventing migration of the valve into the atrium or ventricle. The design of the prosthesis also mimics the native valve and supports a non-round in vivo configuration, which better reproduces native valve function.

In view thereof, disclosed herein are aspects of a valve prosthesis which is generally designed to include a valve body including a plurality of valve leaflets affixed to the skirt and a frame including a distal inflow section, a proximal outflow section, and a valve section between the inflow section and the outflow section. The valve body is attached to the frame in the valve section at a plurality of commissure points. The frame includes a radially repeating cell pattern in the inflow section and the valve section. The outflow section includes a plurality of loops, the loops being attached to the valve section at a plurality of junctions. A plurality of valve section cells are positioned between each junction in a radial direction.

In another exemplary embodiment, disclosed herein are aspects of a valve prosthesis which is generally designed to includes a valve body including a plurality of leaflets affixed to a skirt and a frame including a first tubular structure, a second tubular structure, and a plurality of junctures attaching the first tubular structure to the second tubular structure. The valve body is attached to the frame in the first tubular structure and after implantation of the valve prosthesis in a patient, the first tubular structure is aligned on a first axis and the second tubular structure is aligned on a second axis.

In another exemplary embodiment, disclosed herein are aspects of a method of treating a valve disorder in a patient's heart which generally includes collapsing a valve prosthesis to form attachments at a proximal end of the valve prosthesis engaging attachment tabs connected to a delivery system; delivering the delivery system and valve prosthesis to a heart; expanding the valve prosthesis in the heart such that attachments are not formed; and withdrawing the delivery system from the heart. In the expanded configuration, the valve prosthesis is not engaged with the attachment tabs.

BRIEF DESCRIPTION OF THE DRAWINGS/FIGURES

The accompanying figures, which are incorporated herein, form part of the specification and illustrate embodiments of a valve prosthesis. Together with the description, the figures further serve to explain the principles of and to enable a person skilled in the relevant art(s) to make, use, and implant the valve prosthesis described herein. In the drawings, like reference numbers indicate identical or functionally similar elements.

FIG. 4 is a side view of a valve prosthesis delivery system according to an aspect of this disclosure.

FIG. 5 is a side view of a valve prosthesis delivery system according to an aspect of this disclosure.

DETAILED DESCRIPTION OF THE INVENTION

The following detailed description of a valve prosthesis refers to the accompanying figures that illustrate exemplary embodiments. Other embodiments are possible. Modifications can be made to the embodiments described herein without departing from the spirit and scope of the present invention. Therefore, the following detailed description is not meant to be limiting.

The present invention is directed to a heart valve prosthesis having a self-expanding frame that supports a valve body. The valve prosthesis can be delivered percutaneously to the heart to replace the function of a native valve. For example, the valve prosthesis can replace a bicuspid or a tricuspid valve such as the aortic, mitral, pulmonary, or tricuspid heart valve.

In one aspect of the invention, the valve body comprises three leaflets that are fastened together at enlarged lateral end regions to form commissural joints, with the unattached edges forming the coaptation edges of the valve. The leaflets can be fastened to a skirt, which in turn can be attached to the frame. The upper ends of the commissure points define an outflow or proximal portion of the valve prosthesis. The opposite end of the valve at the skirt defines an inflow or distal portion of the valve prosthesis. The enlarged lateral end regions of the leaflets permit the material to be folded over to enhance durability of the valve and reduce stress concentration points that could lead to fatigue or tearing of the leaflets. The commissural joints are attached above the plane of the coaptation edges of the valve body to minimize the contacted delivery profile of the valve prosthesis. The base of the valve leaflets is where the leaflet edges attach to the skirt and the valve frame.

Figure 1A:
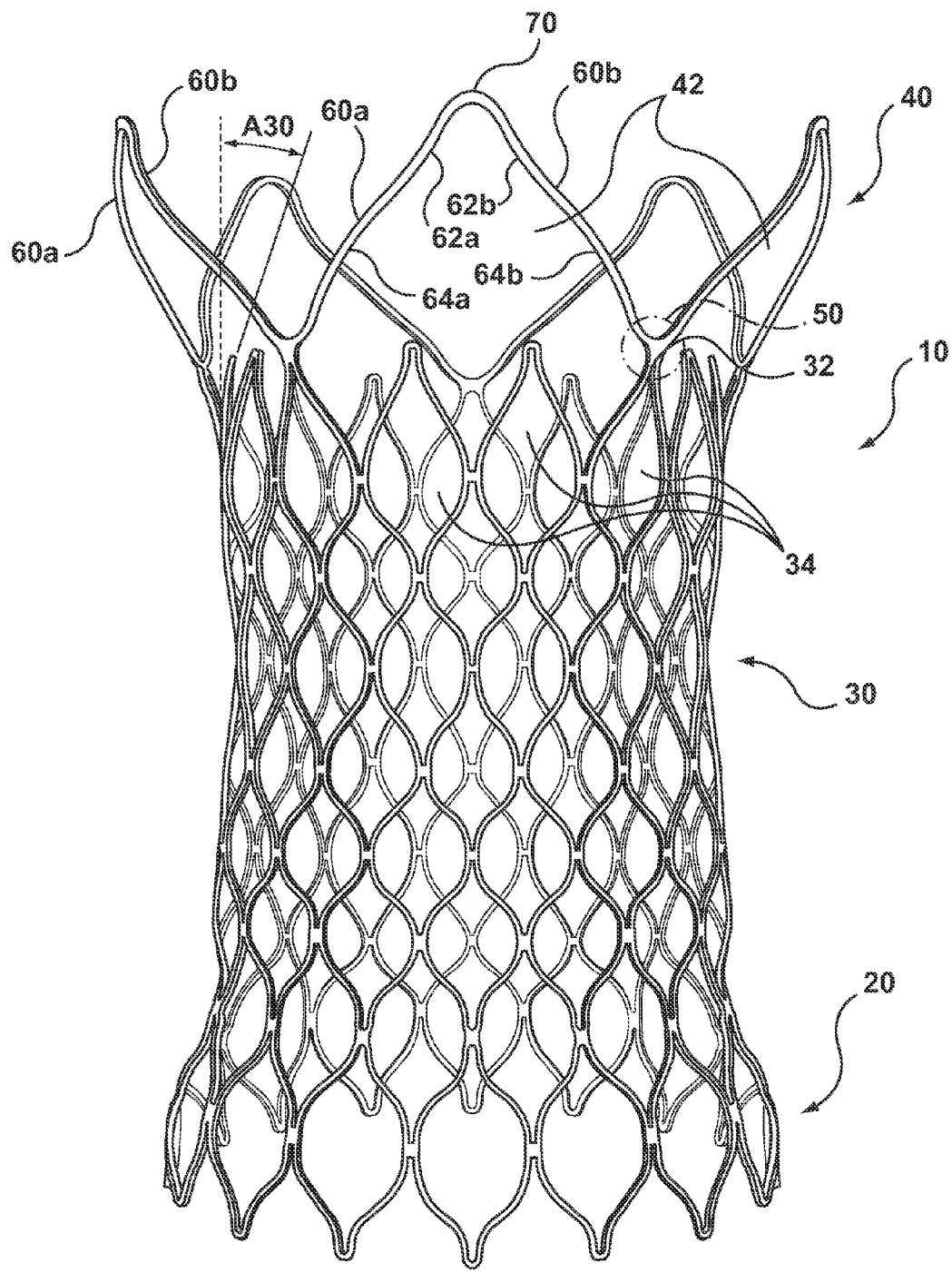
FIG. 1A is a front view of a valve frame, in accordance with an aspect of the disclosure.

Referring now to FIG. 1, frame 10 is an exemplary aspect of the present invention. Frame 10 includes inflow section 20, valve section 30, and outflow section 40. Frame 10 also includes a plurality of cells in inflow section 20 and valve section 30 that can be different sizes and/or shapes.

Figure 1B:
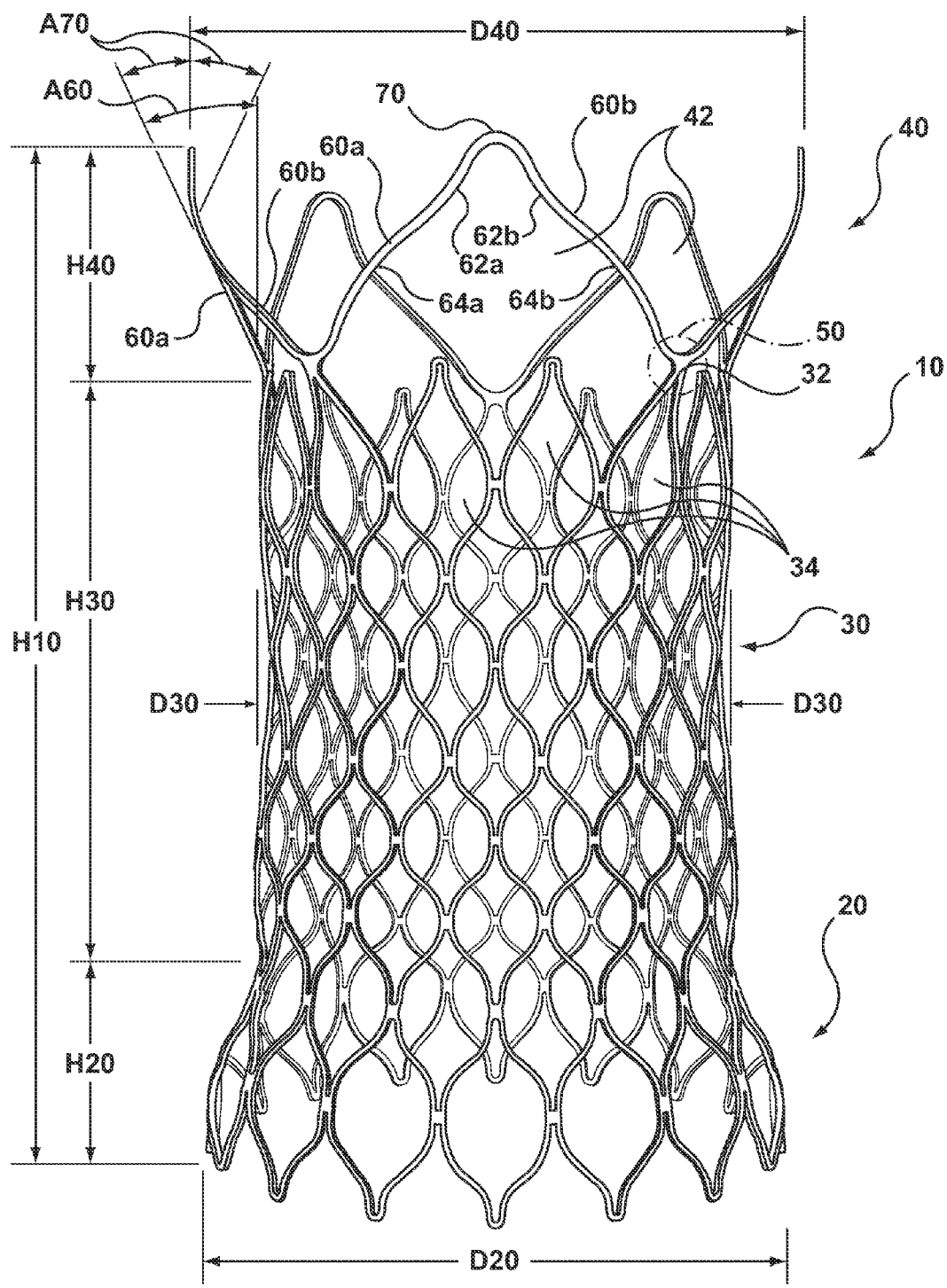
FIG. 1B is a front view of a valve frame, in accordance with an aspect of the disclosure.

The cell pattern permits frame 10 to expand to the shape depicted in FIG. 1, having a conical inflow section 20, an approximately constant diameter valve section 30, and an increased diameter conical outflow section 40. Frame 10 has a total height H10 of approximately 30 mm to approximately 60 mm. In the expanded configuration, the maximum diameter of inflow section 20, D20 shown in FIG. 1B, can range from about 16 mm to about 36 mm, with a preferred range of about 21 to about 33 mm. Inflow section 20 also has a height H20 of approximately 7 mm to approximately 14 mm. The diameter of valve section 30, D30 shown in FIG. 1B, can range from about 18 mm to about 26 mm, with a preferred range of about 20 mm to about 24 mm. Valve section 30 also has a height H30 of approximately 7 mm to approximately 14 mm. The maximum diameter of outflow section 40, D40 shown in FIG. 1B, can range from about 28 mm to about 45 mm, with a preferred range of about 30 mm to about 38 mm. Outflow section 40 also has a height H40 of approximately 10 mm to approximately 25 mm. At the transition between inflow section 20 and valve section 30, frame 10 can have a reduced diameter that is smaller than the diameter of valve section 30. This reduced diameter is designed to abut the natural valve leaflets after valve prosthesis 1 is implanted. This reduced diameter also provides infolding resistance to the frame, allowing for uniform recapture of the device.

Each section of frame 10 in inflow section 20 and valve section 30 has a substantially circular cross-section in the expanded configuration. However, the cell patterns of frame 10 permit frame 10 to adapt to the specific anatomy of the patient, thereby reducing the risk of valve prosthesis migration and reducing the risk of perivalvular leakage. In one aspect of the invention, inflow section 20 of valve prosthesis 1 is disposed in the aortic annulus of the patient's left ventricle while outflow section 40 is positioned in the patient's ascending aorta.

The conical shape of inflow section 20 is designed to form an interference fit with the native valve annulus. The smooth transition from inflow section 20 to valve section 30 is designed to direct blood flow through the valve body with little or no turbulence. Typically, heart valve prostheses aim to create laminar blood flow through the prosthesis in order to prevent lysis of red blood cells, stenosis of the prosthesis, and other thromboembolic complications. Outflow section 40 is designed to conform to a patient's anatomy and to anchor valve prosthesis 1 in the patient's ascending aorta to prevent lateral movement or migration of valve prosthesis 1 due to normal movement of the heart. Outflow section 40 includes outflow loops 42. Each outflow loop 42 is made up of struts 60a and 60b. Struts 60a and 60b come together at edges 70, the proximal most portions of outflow loops 42. Struts 60a and 60b each have proximal concave curves 62a and 62b, respectively, and distal convex curves 64a and 64b, respectively. It is understood that in most embodiments, struts 60a and 60b are made from a unitary laser cut tube of self-expanding metal. In one aspect of the invention, edges 70 are curved. In alternate an alternate aspect of the invention, edges 70 can be straight or angular.

Outflow loops 42 are attached to each other and to valve section 30 at junctions 50. Each junction 50 is made up of a strut 60b from an outflow loop 42, strut 60a from an adjacent outflow loop 42, and a proximal edge or crown 32 of a cell 34 from valve section 30. In a preferred embodiment, junctions 50 are not formed on circumferentially adjacent cells 34 in valve section 30. For example, at least one cell 34 can be positioned between circumferentially adjacent junctions 50. In an alternate aspect of the invention, two or more cells 34 can be positioned between circumferentially adjacent junctions 50. In one aspect of the invention, proximal edges or crowns 32 of cells 34 that are not connected at junctions 50 are angled inward toward the center of frame 10 at an angle A30. Angle A30 can be approximately 0 degrees to approximately 25 degrees. In a preferred embodiment, angle A30 is approximately 10 degrees. Angle A30 helps to retain the valve prosthesis on the delivery system in the collapsed configuration and helps to prevent vascular injury when the valve prosthesis is in the expanded configuration.

Struts 60a and 60b extend outward from junction 50 at an angle A60, shown in FIG. 1B. In one aspect of the invention, angle A60 can be approximately 15 degrees to approximately 80 degrees. In a preferred embodiment, angle A60 is 30 degrees. Edge 70 at the proximal end of struts 60a and 60b can be bent at an angle A70 with respect to the direction of blood flow. In one aspect of the invention, angle A70 can be approximately 15 degrees outward from the center of frame 10 or 15 degrees inward towards the center of frame 10, as shown in FIG. 1B. In a preferred embodiment, angle A70 is 5 degrees inward towards the center of frame 10. Angle A70 is provided to prevent injury to the ascending aorta.

Figure 2:
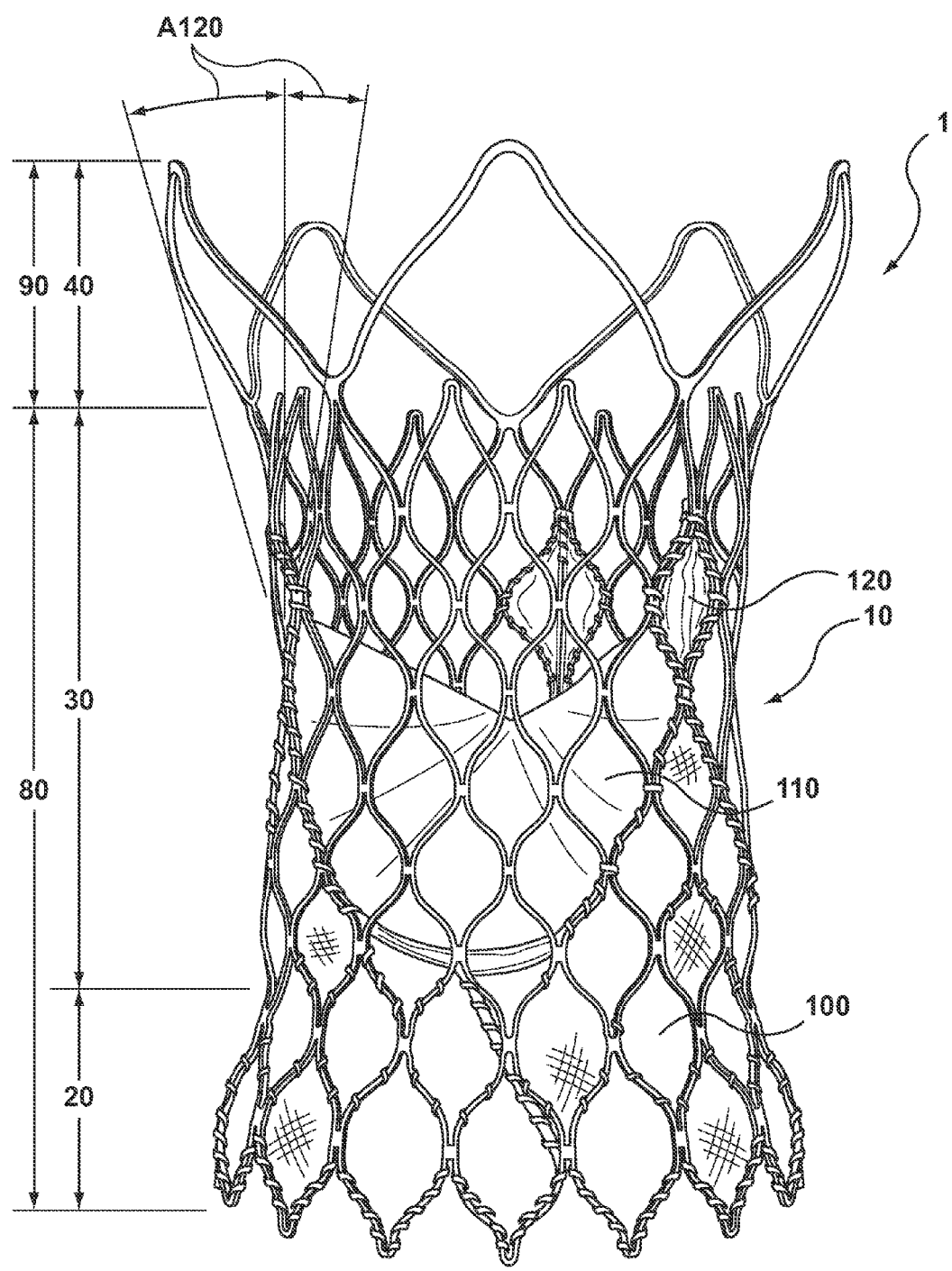
FIG. 2 is a front view of a valve prosthesis, in accordance with an aspect of the disclosure.

Referring now to FIG. 2, valve prosthesis 1 includes frame 10 and valve 100. Valve 100 includes leaflets 110 and commissure points 120. Commissure points 120 are attached to cells of frame 10 in valve section 30. The object of the present valve prosthesis is to mimic the native valve structure. This valve design provides several advantages over other percutaneously delivered replacement valve prostheses. For example, because the diameter of frame 10 in valve section 30 is approximately constant, commissure points 120 can be attached to cells of frame 10 that are approximately parallel to the direction of flow. For example, angle A120 is approximately 0 degrees. This alignment increases the spacing between commissure points 120 and the sinotubular junction which reduces the risk of a coronary occlusion. In addition, the parallel alignment of commissure points 120 along with the size of outflow loops 42 allow a clinician to readily gain access to the coronary arteries, for example, to perform angioplasty or stenting, simply by directing the angioplasty or stent delivery system guidewire through outflow loops 42.

This alignment also reduces stress on commissure points 120 and valve 100 as compared to valve prostheses that include a frame that is angled outward from the center of frame at the commissure attachment points. In an alternate aspect of the invention, the diameter of valve section 30 of frame 10 can be reduced in the region where commissure points 120 attach to frame 10. In this configuration, commissure points 120 can be angled inward towards the center of frame 10. In an alternate aspect of the invention, the diameter of valve section 30 can be increased in the region where commissure points 120 attach to frame 10. In this configuration, commissure points 120 can be angled outwards from the center of frame 10. Consequently, angle A120 can range from approximately 30 degrees outward from the center of the frame to approximately 10 degrees inward towards the center of the frame, as shown in FIG. 2.

In addition, the approximately constant diameter of frame 10 through valve section 30 provides for a reduced force required to crimp valve prosthesis 1 for delivery into the patient's heart, as compared to prior art valve prostheses. Such a configuration also reduces the strain on frame 10 in the collapsed configuration.

An additional advantage of this frame design is the ability to isolate deformation caused by positioning of the valve prosthesis in situ along different portions of frame 10. As discussed above, outflow section 40 is composed of a plurality of outflow loops 42 and junctions 50 are not present on circumferentially adjacent cells 34 of valve section 30. Therefore, outflow loops 42 span at least one cell 34 of valve section 30 in a circumferential direction and have a limited number of junctions 50 which connect outflow section 40 to valve section 30. Accordingly, the amount of frame material that makes up outflow section 40 is reduced, as compared to a frame where the cellular structure extends circumferentially throughout the entire frame. This reduction in material along with the reduced number of connections between outflow section 40 and valve section 30 allows outflow section 40 to be flexible and provides for a more distal bending point on frame 10. This provides for reduced transmission of the deformation along frame 10, allowing valve section 30 to maintain a circular shape in situ.

Figure 3:
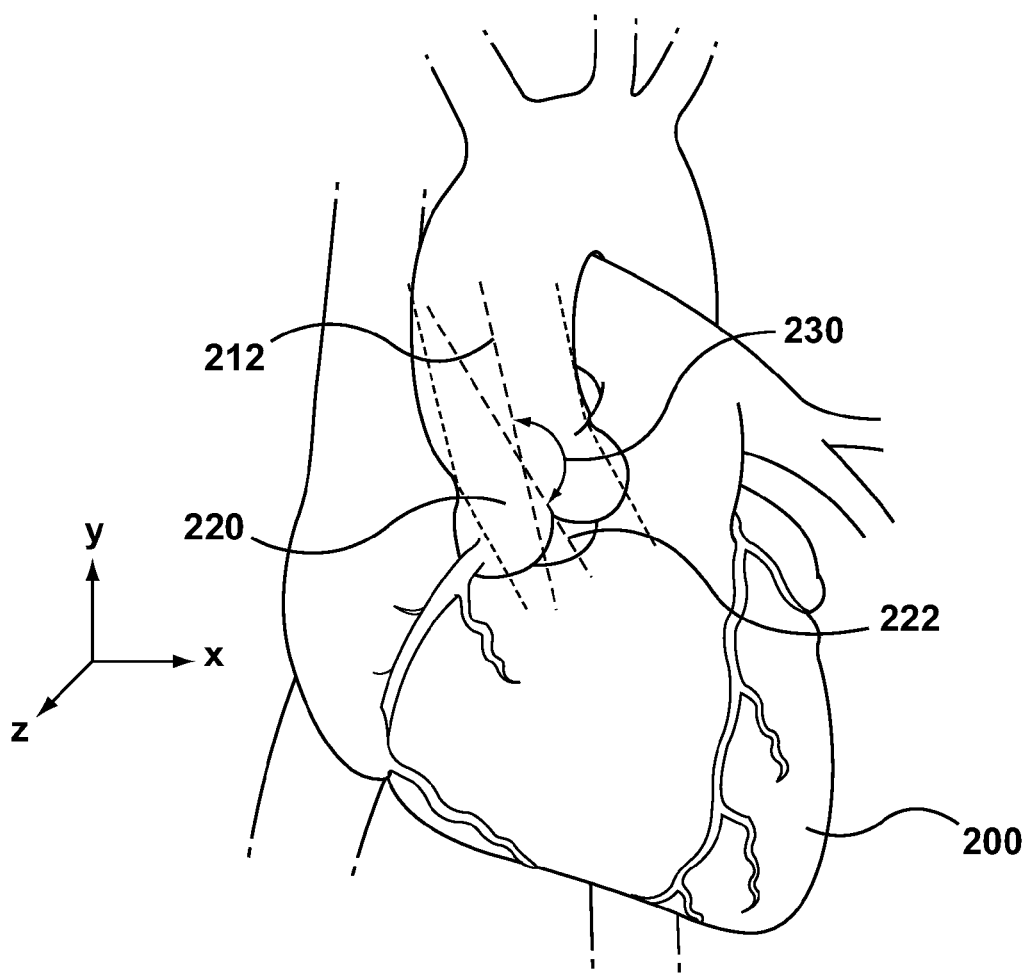
FIG. 3 is a front view of a human heart.

In a typical heart 200, shown in FIG. 3, aorta 210 has an aortic axis 212. Aorta 210 also contains a native valve 220 and a sinus axis 222. Sinus axis 222 is offset from aortic axis 212 such that aortic axis 212 and sinus axis 222 are not parallel. This offset is shown in the X-Y plane in FIG. 3, and is represented as angle 230. The aorta is an asymmetric structure and the aortic axis and sinus axis can also be offset in the Y-Z and X-Z planes.

As discussed above, outflow section 40 anchors valve prosthesis 1 in the patent's ascending aorta. The aorta deforms outflow section 40 which can transmit a force along frame 10. It is the inventors understanding that prior art frame structures are rigid along the entire frame from the outflow to the inflow portion of the frame, causing this force to deform the entire frame structure. Such deformation along the entire frame prevents the frame from properly aligning on either the aortic axis or the sinus axis. To address this issue, in one aspect of the disclosure, the structure and flexibility of frame 10, particularly in outflow section 40, provides a more distal bending point on the frame to allow valve section 30 to align on sinus axis 222 during deployment, while outflow section 40 simultaneously aligns on aortic axis 212. Because valve section 30 is aligned on sinus axis 222, valve 100 is able to form a competent seal with the native valve 220 which reduces leakage around valve prosthesis 1. In effect, the present frame design creates two tubular structures, as shown in FIG. 2. First tubular structure 80 includes inflow section 20 and valve section 30. Second tubular structure 90 includes outflow section 40. The proximal most portion of first tubular structure 80 is attached to the distal most portion of second tubular structure 90 at junctions 50. Junctions 50 create a flexible juncture between the tubular structures allowing first tubular structure 80 to align with sinus axis 222 while second tubular structure 90 aligns with the aortic axis 212. After implantation in a patient, first tubular structure 80 can be offset from second tubular structure 90 in the axial direction.

In addition, the forces exerted by the aorta on a valve prosthesis create pressure that is transmitted from the outflow portion of the frame to the inflow portion of the frame located near the left bundle branch. This pressure can cause conduction disturbances in the left bundle branch resulting in the need for a patient to receive a permanent pacemaker. The flexibility and structure of outflow section 40 absorbs the forces exerted by the aorta on frame 10. This design reduces the pressure exerted by the aorta along valve prosthesis 1 and can prevent the need for a pacemaker in the patient. In particular, the flexible juncture between first tubular structure 80 and second tubular structure 90 prevent forces exerted on second tubular structure 90 from transferring to first tubular structure 80.

Prior art valve prostheses typically have eyelets to attach the valve prostheses to a delivery system. The eyelets attach to tabs which retain the valve prosthesis. However, the attachment between the eyelets and the tabs provides minimal clearance when the valve prosthesis is deployed. As a result, the geometry of the attachment mechanism and the torque generated by advancing the delivery system around the curvature of the aortic arch can cause the valve to lock with the delivery system preventing full deployment of the valve prosthesis in the patient's heart. This is especially a problem when after delivery, one of the tabs remains pressed against the aortic wall. When this occurs, there can be insufficient clearance for the eyelet to fully detach from the tabs and delivery system. To release the valve, the delivery system must be moved and turned which can interfere with the correct positioning of the valve prosthesis.

In addition, delivery systems typically include an outer sheath or capsule that surrounds the collapsed valve prosthesis during delivery to the implantation site. During deployment, the capsule is withdrawn over the valve prosthesis. The friction between the capsule and the valve prosthesis during capsule withdrawal imposes an axial force along the valve prosthesis which can cause the valve prosthesis to improperly migrate on the delivery system. Accordingly, the delivery system must have sufficient structure to hold the valve prosthesis in place and to resist the axial force created by withdrawal of the capsule during deployment of the valve prosthesis.

Frame 10 provides an integrated attachment system that ensures the full release of valve prosthesis 1 from the delivery system. The design utilizes the self-expanding nature of the frame to detach the valve prosthesis from the delivery system. In the collapsed configuration, frame 10 forms an attachment to the delivery system. When the frame expands, the attachment is no longer present.

Figure 6:
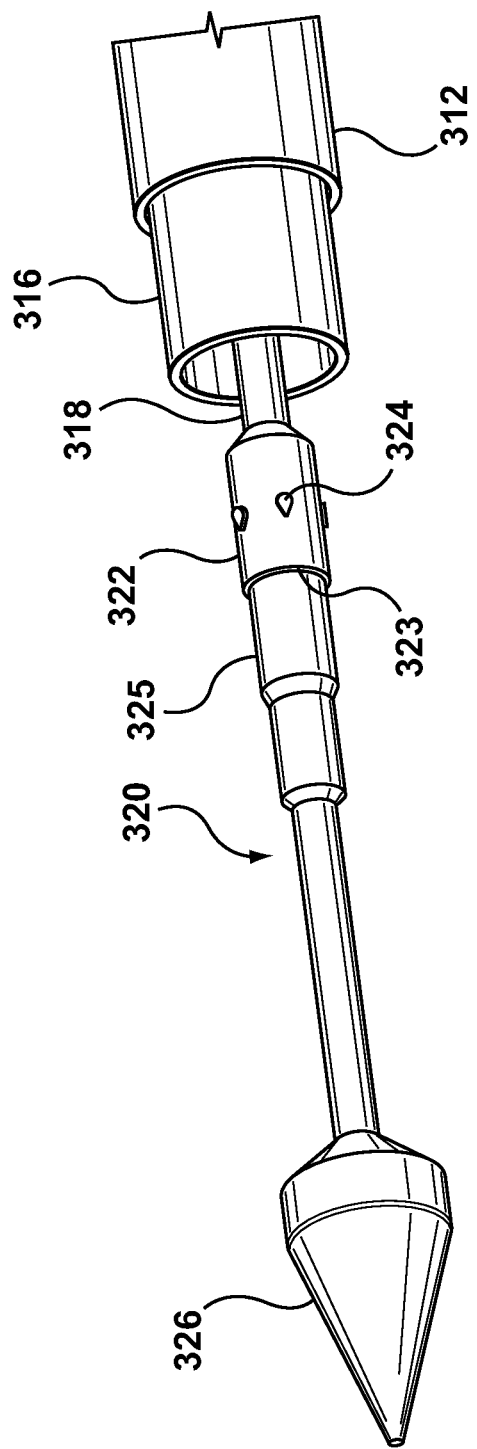
FIG. 6 is a perspective view of a valve prosthesis delivery system according to an aspect of this disclosure.

Referring now to FIGS. 4-6, the delivery system for valve prosthesis 1 includes catheter assembly 310 that includes an outer sheath 312, a pusher tube 314, and a central tube 318, each of which are concentrically aligned and permit relative motion with respect to each other. At a distal end of pusher tube 314 is a capsule 316. At a distal end of central tube 318 is plunger assembly 320. Capsule 316 surrounds plunger assembly 320 during delivery of valve prosthesis 1. Plunger assembly 320 includes hub 322 at a proximal end and tip 326 at a distal end. The diameter of hub 322 is larger than the diameter of section 325. The step change at edge 323 is provided to abut the proximal edges or crowns 32 of cells 34 in valve section 30 in the collapsed configuration. During capsule withdrawal, edge 323 will apply back pressure to proximal edges or crowns 32 of cells 34 to prevent migration of the valve prosthesis on the delivery system. In the collapsed configuration, angle A30 of cells 34 further helps to maintain engagement with edge 323 during deployment of the valve prosthesis. Tip 326 facilitates the advancement of catheter assembly 310 through the patient's vasculature. Hub 322 includes one or more tabs 324 for retaining valve prosthesis 1 on plunger assembly 320. Tabs 324 also prevent the pre-release of valve prosthesis 1 and assist in retaining valve prosthesis 1 during recapture. The top surface of tabs 324 interact with the inner surface of capsule 316 to form an interference fit.

Figure 7:
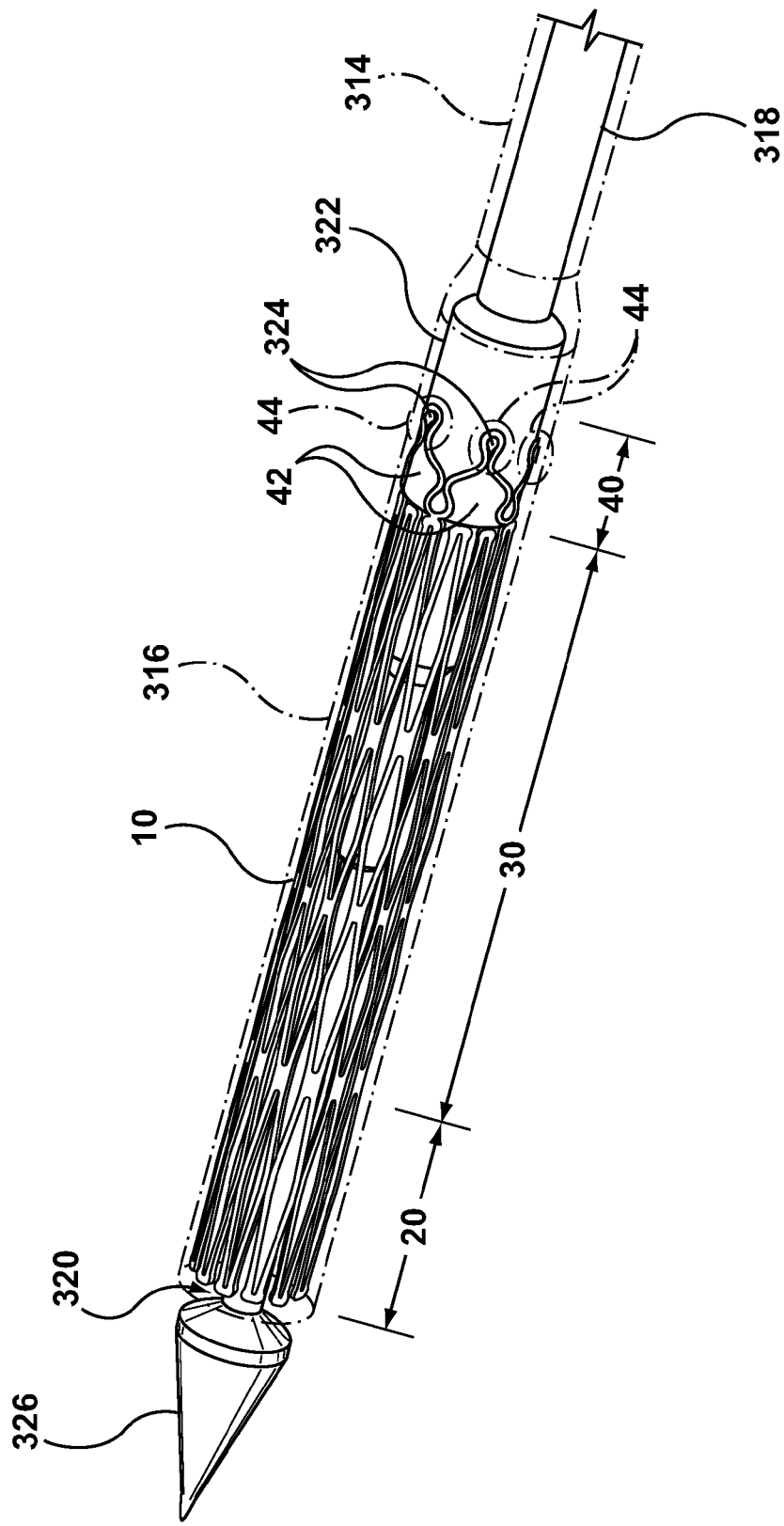
FIG. 7 is a perspective view of a valve prosthesis and valve prosthesis delivery system according to an aspect of this disclosure.
Figure 8:
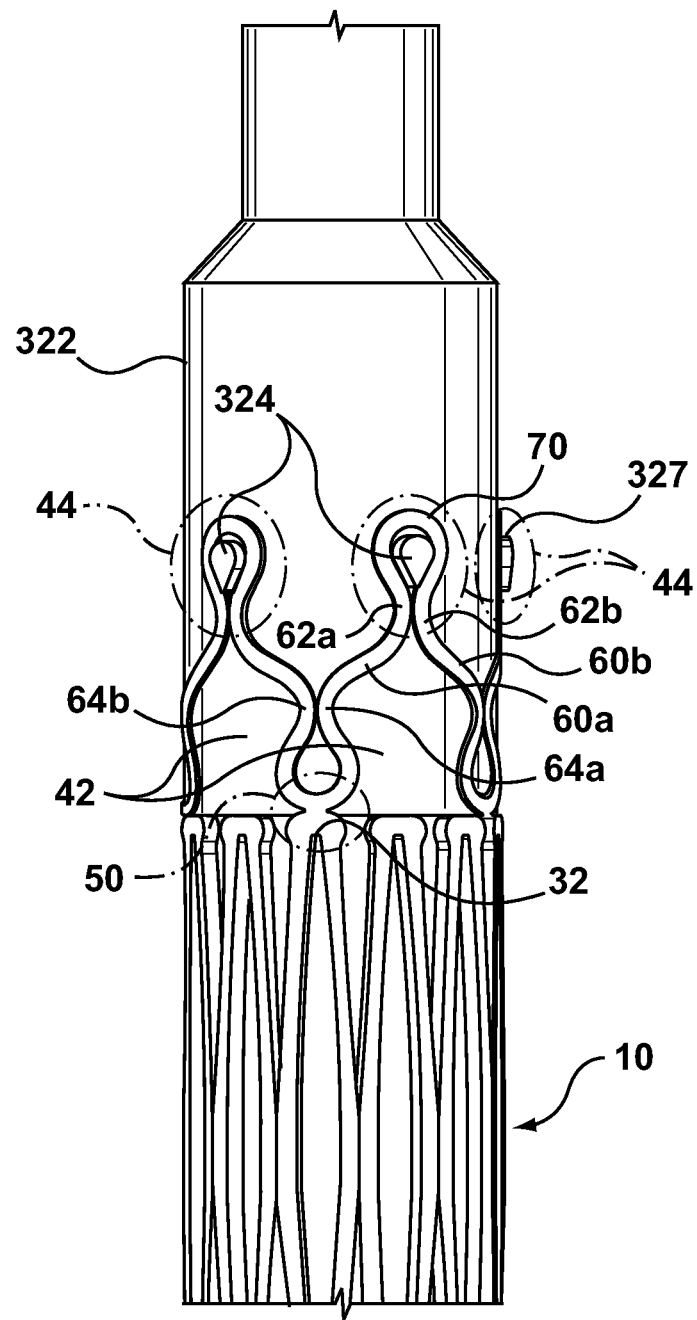
FIG. 8 is a front view of a valve prosthesis and valve prosthesis delivery system according to an aspect of this disclosure.

FIGS. 7 and 8 show collapsed valve prosthesis 1 attached to plunger assembly 320. In a collapsed configuration, the circumferential distance between concave curves 62a and 62b on struts 60a and 60b of outflow loops 42 is reduced to form attachment loops 44 between concave curves 62a and 62b and edge 70. In one aspect of the invention, concave curves 62a and 62b on struts 60a and 60b on collapsed valve prosthesis 1 touch to form a closed attachment loop. This closed attachment loop increases the column strength of outflow section 40 in the collapsed configuration, as compared to when concave curves 62a and 62b do not touch. This increased column strength can be required to prevent outflow section 40 from buckling during withdrawal of capsule 316 during delivery of valve prosthesis 1. Alternatively, a gap can be present between concave curves 62a and 62b on struts 60a and 60b on collapsed valve prosthesis 1. Tabs 324 on plunger assembly 320 engage attachment loops 44 during delivery of valve prosthesis 1. Capsule 316 surrounds plunger assembly 320 and collapsed valve prosthesis 1 and restrains valve prosthesis 1 in the radial direction. The engagement between tabs 324 and attachment loops 44 prevents migration of valve prosthesis 1 on plunger assembly 320 in the axial direction. For example, the engagement between tabs 324 and attachment loops 44 can prevent pre-release of valve prosthesis 1 from the delivery system. This engagement can also allow for recapture of valve prosthesis 1 if valve prosthesis 1 needs to be repositioned. The interference fit between the top surface of tabs 324 and the inner surface of capsule 316 prevents attachment loops 44 from moving over tabs 324 and disengaging from plunger assembly 320.

Figure 9:
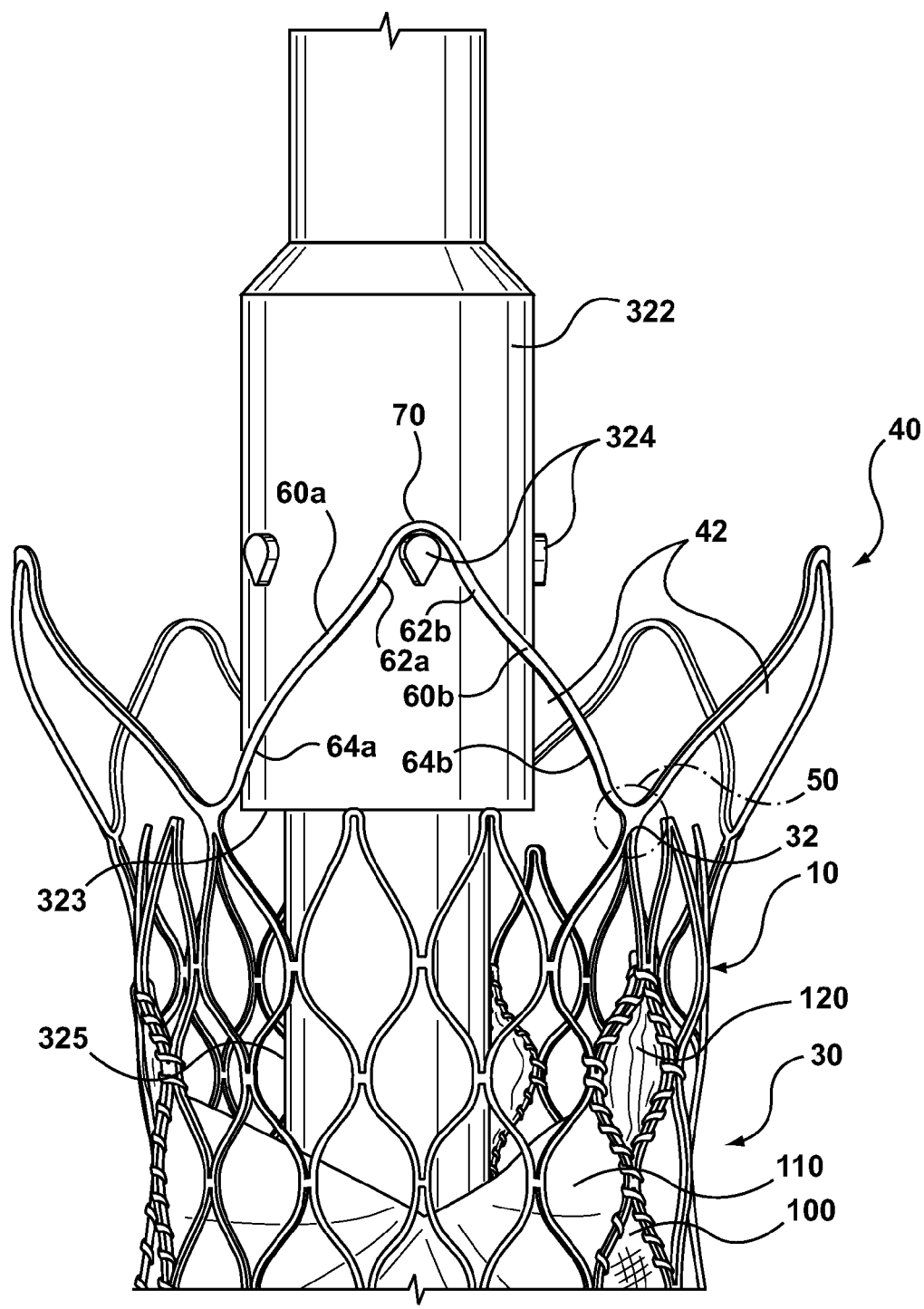
FIG. 9 is a front view of a valve prosthesis and valve prosthesis delivery system according to an aspect of this disclosure.
Figure 10A:
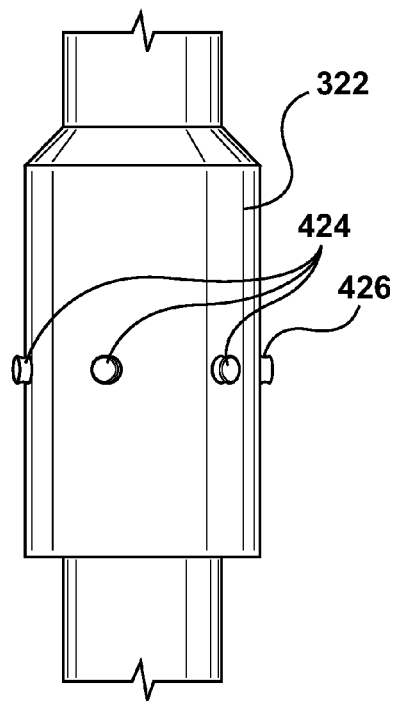
FIG. 10a is a front view of a valve prosthesis delivery hub according to an alternate aspect of this disclosure.
Figure 10B:
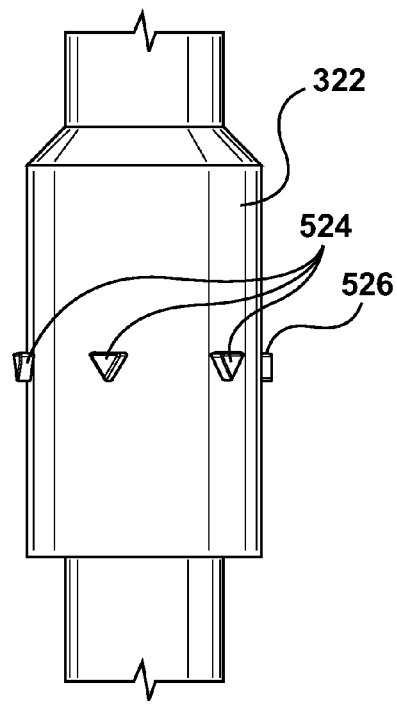
FIG. 10b is a front view of a valve prosthesis delivery hub according to an alternate aspect of this disclosure.
Figure 10C:
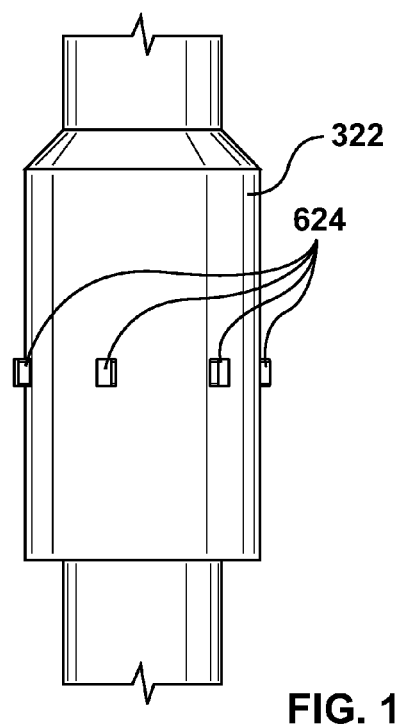
FIG. 10c is a front view of a valve prosthesis delivery hub according to an alternate aspect of this disclosure.
Figure 10D:
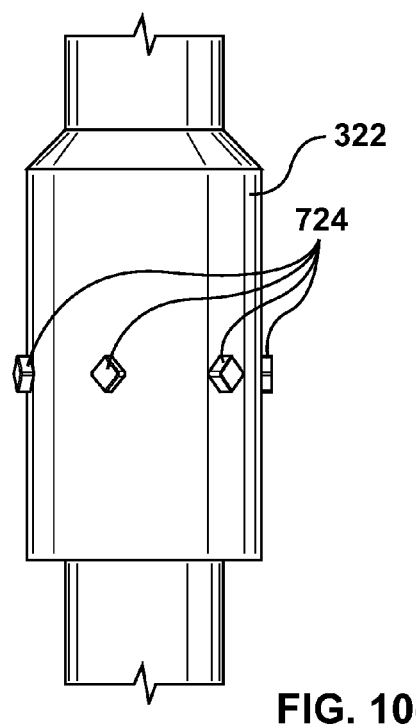
FIG. 10d is a front view of a valve prosthesis delivery hub according to an alternate aspect of this disclosure.

In one aspect of the invention, FIG. 9 shows frame 10 in the expanded configuration. In the expanded configuration, the circumferential distance between concave curves 62a and 62b is increased and concave curves 62a and 62b no longer form attachment loops with edges 70. Accordingly, valve prosthesis 1 is disengaged from tabs 324 on the delivery system. In the expanded configuration of frame 10, the attachment feature securing valve prosthesis 1 to the delivery system is no longer present. This design ensures that the valve can be fully released from the delivery system.

Referring now to FIGS. 8-10d, tabs 324 on hub 322 can be teardrop shaped. In alternate aspects of the invention shown in FIGS. 10a-10d, the tabs may be any other shape known to a person of ordinary skill in the art. For example, tabs 424 are circular; tabs 524 are triangular, tabs 624 are rectangular, and tabs 724 are square. In one aspect of the invention, perimeter surface 327 on tabs 324 is flat and perpendicular to the direction of blood flow. In an alternate aspect, perimeter surface 426 of tabs 424 is a concave curve. In a further aspect of the invention, perimeter surface 526 of tabs 524 is a convex curve. The shape of the perimeter surface of the tabs can be optimized to allow edge 70 to clear the tabs during delivery system withdrawal, and to prevent edge 70 from slipping over the tabs prematurely. In addition, the front surface of the tabs can be flat. In an alternate aspect, the front surface of the tabs can be a convex curve.

Figures 11, 12:
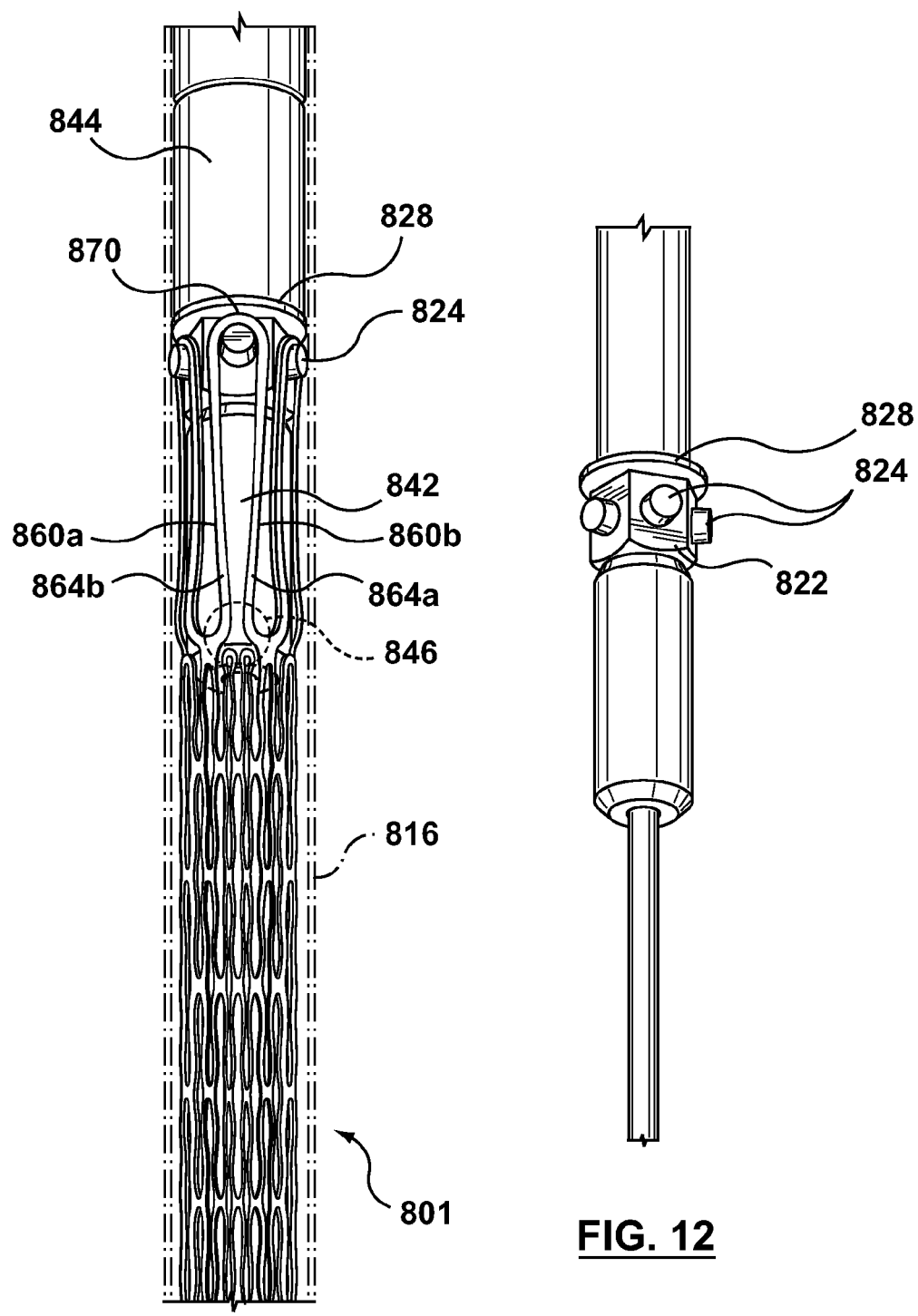
FIG. 11 is a front view of a valve prosthesis and valve prosthesis delivery system according to an alternate aspect of this disclosure.
FIG. 12 is a front view of a valve prosthesis delivery system according to an alternate aspect of this disclosure.

FIGS. 11 and 12 illustrate an alternate frame and delivery system design. As discussed above, a gap can be present between the concave curves and/or the convex curves of the struts of the frame in the collapsed configuration. As shown in FIG. 11, struts 860a and 860b of outflow loops 842 do not touch in the collapsed configuration. Gap 846 is provided between struts 860a and 860b in the collapsed configuration. Shelf 828 is provided on hub 822 to prevent migration of valve prosthesis 801 on the delivery system during deployment. In the collapsed configuration, edge 870 of valve prosthesis 801 is secured between shelf 828 and tabs 824 on hub 822. Shelf 828 applies back pressure to frame edge 870 during withdrawal of capsule 816 and deployment of the valve prosthesis 801. Tabs 824 pull valve prosthesis 801 during recapture.

Figure 13:
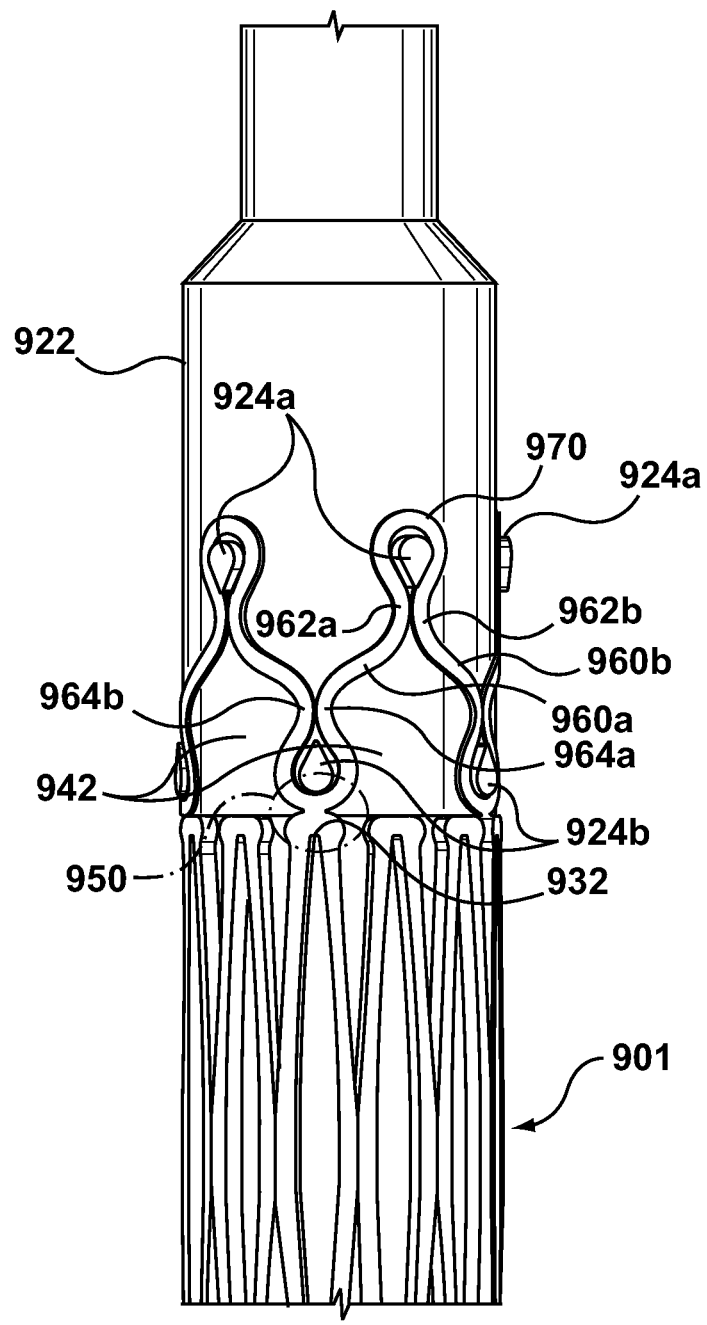
FIG. 13 is a front view of a valve prosthesis and valve prosthesis delivery system according to an alternate aspect of this disclosure.

An alternate embodiment is shown in FIG. 13. FIG. 13 shows hub 922 including a first row of tabs 924a and a second row of tabs 924b. Tabs 924b are provided to prevent migration of valve prosthesis 901 on the delivery system during deployment. For example, during withdrawal of the capsule, tabs 924b apply back pressure to junctures 950 on valve prosthesis 901. Tabs 924b serve a similar function as shelf 828, discussed above. In this embodiment, tabs 924a pull valve prosthesis 901 during recapture.

The valve prosthesis can replace the function of a tricuspid or bicuspid heart valve including the mitral valve, the aortic valve, the pulmonary valve, or the tricuspid valve. The valve can be delivered, for example, transfemorally, transseptally, transapically, transradially, or transatrially.

Implantation of the valve prosthesis will now be described. As discussed above, the valve prosthesis preferably comprises a self-expanding frame that can be compressed to a contracted delivery configuration onto an inner member of a delivery catheter. This frame design requires a loading system to crimp valve prosthesis 1 to the delivery size, while allowing the proximal end of valve prosthesis 1 to protrude from the loading system so that the proximal end can be attached to tabs 324.

The valve prosthesis and inner member can then be loaded into a delivery sheath of conventional design, e.g., having a diameter of less than 20-24 French. Due in part to the fact that the commissure points are longitudinally offset from the coaptation edges of the leaflets, and due to the ability to maintain a lower commissure height, it is expected that the valve prosthesis can achieve a significantly smaller delivery profile than previously-known percutaneously-deliverable replacement valves.

The delivery catheter and valve prosthesis can then be advanced in a retrograde manner through the femoral artery and into the patient's descending aorta. The catheter then is advanced, under fluoroscopic guidance, over the aortic arch, through the ascending aorta and mid-way across the defective aortic valve. Once positioning of the catheter is confirmed, capsule 316 can be withdrawn proximally, thereby permitting valve prosthesis 1 to self-expand.

As the valve prosthesis expands, it traps the leaflets of the patient's defective aortic valve against the valve annulus, retaining the native valve in a permanently open state. The outflow section of the valve prosthesis expands against and aligns the prosthesis within the ascending aorta, while the inflow section becomes anchored in the aortic annulus of the left ventricle, so that the skirt reduces the risk of perivalvular leaks.

Alternatively, the valve prosthesis can be delivered through a transapical procedure. In a transapical procedure, a trocar or overtube is inserted into the left ventricle through an incision created in the apex of a patient's heart. A dilator is used to aid in the insertion of the trocar. In this approach, the native valve (e.g. the mitral valve) is approached from the downstream relative to the blood flow. The trocar is retracted sufficiently to release the self-expanding valve prosthesis. The dilator is preferably presented between the valve leaflets. The trocar can be rotated and adjusted as necessary to properly align the valve prosthesis. The dilator is advanced into the left atrium to begin disengaging the proximal section of the valve prosthesis from the dilator.

In an alternate aspect of the invention, the valve prosthesis can be delivered through a transatrial procedure. In this procedure, the dilator and trocar are inserted through an incision made in the wall of the left atrium of the heart. The dilator and trocar are advanced through the native valve and into the left ventricle of heart. The dilator is then withdrawn from the trocar. A guide wire is advanced through the trocar to the point where the valve prosthesis comes to the end of the trocar. The valve prosthesis is advanced sufficiently to release the self-expanding frame from the trocar. The trocar can be rotated and adjusted as necessary to properly align the valve prosthesis. The trocar is completely withdrawn from the heart such that the valve prosthesis self-expands into position and assumes the function of the native valve.

The foregoing description has been presented for purposes of illustration and enablement, and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A valve prosthesis comprising:
a valve body including a plurality of valve leaflets affixed to a skirt; and
a frame including a distal inflow section, a proximal outflow section, and a valve section between the inflow section and the outflow section, wherein:
the valve body is attached to the frame in the valve section at a plurality of commissure points,
the frame includes a circumferentially repeating cell pattern in the inflow section and the valve section,
the outflow section includes a plurality of loops, the plurality of loops being attached to a proximal row of circumferentially repeating cells of the valve section at a plurality of junctions,
wherein each of the plurality of loops includes a respective first strut and a respective second strut joined proximally at a loop edge, with the first strut being attached distally to a proximal crown of a respective first cell of the proximal row of cells of the valve section at a respective first junction of the plurality of junctions and with the second strut being attached distally to a proximal crown of a respective second cell of the proximal row of cells of the valve section at a respective second junction of the plurality of junctions,
wherein a plurality of circumferentially adjacent cells in the proximal row of cells of the valve section are positioned entirely between the first and second junctions of each loop in a circumferential direction, with proximal crowns of the plurality of circumferentially adjacent cells being unattached to the outflow section, and
wherein the valve section is distal to the outflow section and a proximal-most end of the commissure points is distal to the proximal crowns of the plurality of circumferentially adjacent cells of the proximal row of cells.

2. The valve prosthesis of claim 1, wherein the plurality of loops includes a first loop, a second loop and a third loop,
wherein the first junction of the first loop corresponds to the second junction of the second loop such that the first loop and the second loop are connected to the proximal row of cells of the valve section at a first common crown of the proximal row of cells of the valve section that is the crown of first cell corresponding to the first loop and the second cell corresponding to the second loop, and
wherein the first junction of the second loop corresponds to the second junction of the third loop such that the second loop and the third loop are connected to the proximal row of cells of the valve section at a second common crown of the proximal row of cells of the valve section that is the crown of the first cell corresponding to the second loop and the second cell corresponding to the third loop.

3. A valve prosthesis comprising:
a valve body including a plurality of valve leaflets affixed to a skirt; and
a frame including a distal inflow section, a proximal outflow section, and a valve section between the inflow section and the outflow section, wherein:
the valve body is attached to the frame in the valve section at a plurality of commissure points, the frame includes a circumferentially repeating cell pattern in the inflow section and the valve section, the outflow section includes a plurality of loops, the plurality of loops being attached to a proximal row of circumferentially repeating cells of the valve section at a plurality of junctions, wherein each of the plurality of loops includes a respective first strut and a respective second strut joined proximally at a loop edge, with the first strut being attached distally to a proximal crown of a respective first cell of the proximal row of cells of the valve section at a respective first junction of the plurality of junctions and with the second strut being attached distally to a proximal crown of a respective second cell of the proximal row of cells of the valve section at a respective second junction of the plurality of junctions, wherein a plurality of circumferentially adjacent cells in the proximal row of cells of the valve section are positioned entirely between each of the first and second junctions of a respective loop in a circumferential direction with proximal crowns of the plurality of circumferentially adjacent cells being unattached to the outflow section, and wherein in a collapsed configuration of the frame, a portion of the first strut of each loop touches a portion of the second strut of the respective loop to form a closed attachment loop between the first strut, the second strut, and the loop edge of each respective loop, and wherein the portions of the first strut and the second strut which touch each other in the collapsed configuration do not touch each other in a deployed configuration of the frame.

4. The valve prosthesis of claim 1, wherein the plurality of circumferentially adjacent cells in the proximal row of cells of the valve section is two valve section cells being positioned between the first and second junctions of each loop in a circumferential direction.

5. The valve prosthesis of claim 3, wherein:
the first strut of each of the plurality of loops includes a first concave curve and the second strut of each of the plurality of loops includes a second concave curve, and
in the collapsed configuration, the first concave curve of each loop touches the second concave curve of the respective loop.

6. The valve prosthesis of claim 3, wherein the closed attachment loop is configured to surround and engage an attachment tab on a valve prosthesis delivery system.

7. A valve prosthesis for deploying within a native aortic heart valve comprising:
a valve body including a plurality of leaflets affixed to a skirt; and
a single lumen frame including,
a first tubular structure having a first axis,
a second tubular structure having a second axis, the second tubular structure including a plurality of loops wherein each of the plurality of loops includes a first strut and a second strut joined proximally at a loop edge and joined distally to respective first and second junctions of a plurality of junctions that attach the first tubular structure to the second tubular structure, the plurality of junctions forming bending points between the first tubular structure and the second tubular structure, wherein in a collapsed configuration of the frame, the first strut and the second strut of each loop each includes four curves, a first curve, a second curve, a third curve, and a fourth curve, wherein the first curve is disposed between one of the first and second junctions and the second curve, the second curve is disposed between the first curve and the third curve, the third curve is disposed between the second curve and the fourth curve, and the fourth curve is disposed between the third curve and the loop edge, wherein the third curve of each of the first strut and the second strut of one of the plurality of loops touch each other when the frame is in the collapsed configuration and do not touch each other in a deployed configuration of the frame, wherein the valve body is attached to the frame in the first tubular structure, and wherein in the deployed configuration the second tubular structure is configured to bend from the first tubular structure at the plurality of junctions such that the first axis of the first tubular structure generally aligns on a sinus axis of a native aortic heart valve and the second axis of the second tubular structure generally aligns on an aortic axis of an aorta with the second axis being offset at an angle from the first axis.

8. The valve prosthesis of claim 7, wherein the first tubular structure is substantially rigid.

9. The valve prosthesis of claim 7, wherein
the plurality of leaflets are attached to the first tubular structure at a plurality of commissure points, and
the first tubular structure is distal to the second tubular structure and the plurality of commissure points are distal to the plurality of junctions.

10. The valve prosthesis of claim 7, wherein deformation of the second tubular structure does not substantially deform the first tubular structure.

11. The valve prosthesis of claim 7, wherein
the plurality of loops includes a first loop, a second loop, and a third loop,
the first junction of the first loop corresponds to the second junction of the second loop such that the first strut of the first loop and the second strut of the second loop are connected to the first tubular structure at a first crown of an edge of the first tubular structure, and
the first junction of the second loop corresponds to the second junction of the third loop such that the first strut of the second loop and the second strut of the third loop are connected to the first tubular structure at a second crown of the edge of the first tubular structure.

12. The valve prosthesis of claim 7, wherein each loop is configured to surround and engage an attachment tab on a valve prosthesis delivery system with the frame in the collapsed configuration.

13. The valve prosthesis of claim 7, wherein the second tubular structure includes at least four loops.

14. The valve prosthesis of claim 7, wherein the first curve and the third curve are curved in a first direction and the second curve and the fourth curve are curved in a second direction generally opposite the first direction.

15. The valve prosthesis of claim 7, wherein the second curve of the first strut of a first one of the plurality of loops touches the second curve of the second strut of an adjacent one of the plurality of loops.

* * * * *